United States Patent
Stetter et al.

(10) Patent No.: US 9,213,016 B1
(45) Date of Patent: Dec. 15, 2015

(54) AUTOMATED SELF-COMPENSATION APPARATUS AND METHODS FOR PROVIDING ELECTROCHEMICAL SENSORS

(71) Applicant: KWJ Engineering Inc., Newark, CA (US)

(72) Inventors: Joseph R. Stetter, Hayward, CA (US); Melvin Findlay, Buchanan, GA (US); Bennett J. Meulendyk, Dublin, CA (US)

(73) Assignee: SPEC Sensors, LLC, Newark, CA (US)

( * ) Notice: Subject to any disclaimer, the term of this patent is extended or adjusted under 35 U.S.C. 154(b) by 0 days.

(21) Appl. No.: 14/465,278

(22) Filed: Aug. 21, 2014

(51) Int. Cl.
*G01N 27/49* (2006.01)

(52) U.S. Cl.
CPC ...................................... *G01N 27/49* (2013.01)

(58) Field of Classification Search
CPC .......... G01N 33/0006; G01N 33/0008; G01N 33/0009; G01N 33/0004; G01N 33/0036–33/0045; G01N 27/49
USPC .......... 204/400, 401, 406, 431; 205/781, 782, 205/775, 785.5
See application file for complete search history.

(56) References Cited

U.S. PATENT DOCUMENTS

| | | | |
|---|---|---|---|
| 5,716,506 A | 2/1998 | Maclay et al. | |
| 6,090,268 A * | 7/2000 | Kunimatsu et al. | 205/782 |
| 7,168,288 B2 | 1/2007 | Eickhoff et al. | |
| 7,687,163 B2 | 3/2010 | Sinha et al. | |
| 7,887,683 B2 | 2/2011 | Dalmia et al. | |
| 8,543,340 B2 | 9/2013 | Tice | |
| 2006/0042960 A1 * | 3/2006 | Tice | 205/775 |

FOREIGN PATENT DOCUMENTS

WO 03038421 5/2003

* cited by examiner

*Primary Examiner* — J. Christopher Ball
*Assistant Examiner* — Maris R Kessel
(74) *Attorney, Agent, or Firm* — Dinsmore & Shohl LLP

(57) ABSTRACT

Systems and methods for automated self-compensation are described herein. Accordingly, some embodiments of a method may include measuring a signal from an electrochemical sensor device, where the signal relates to the presence of a predetermined gas, and where the electrochemical sensor device includes a potentiostat, measuring an internal property of the electrochemical sensor device by electronically pinging the potentiostat, and receiving a response from the potentiostat. In some embodiments, the method may include interpreting the response through an associative relationship between the electrochemical sensor device and a data acquisition and calculation module, determining an effect of an environmental factor from the response, compensating for effects of the environmental factor by adjusting the signal from the electrochemical sensor device and outputting the adjusted signal.

18 Claims, 11 Drawing Sheets

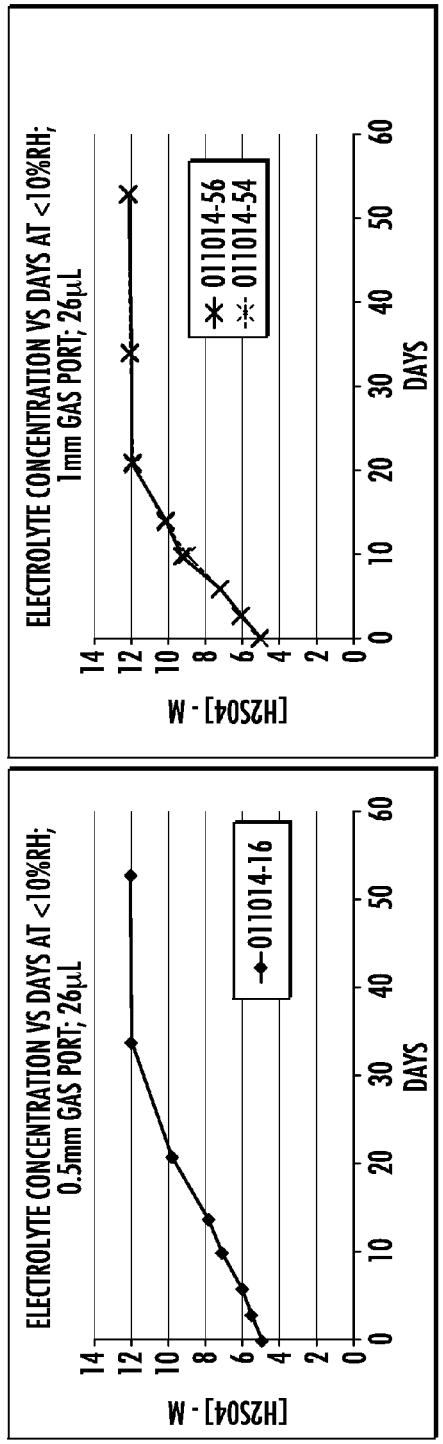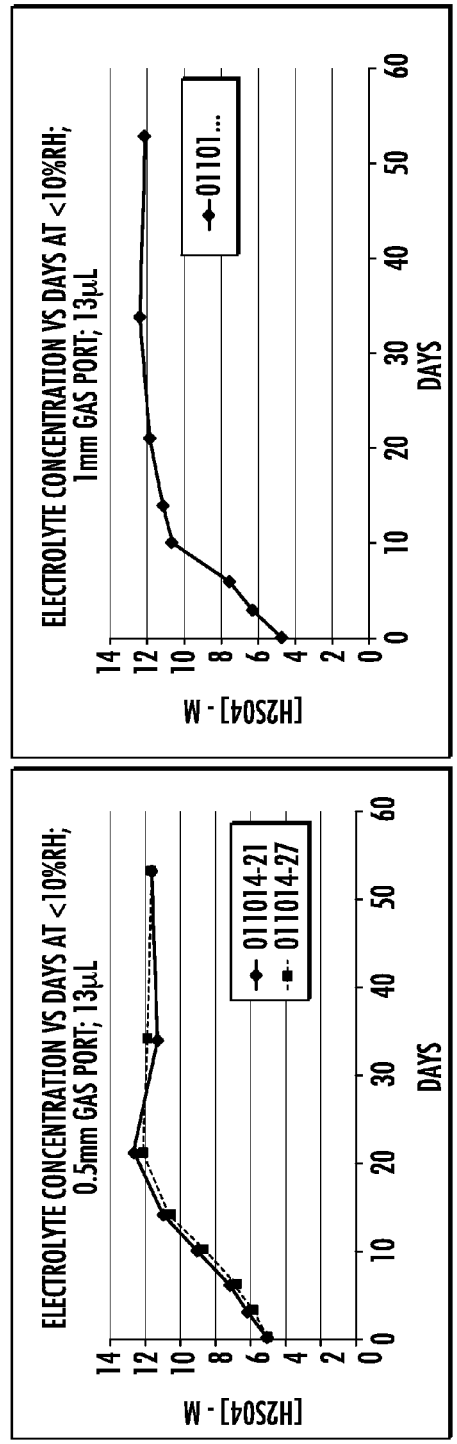

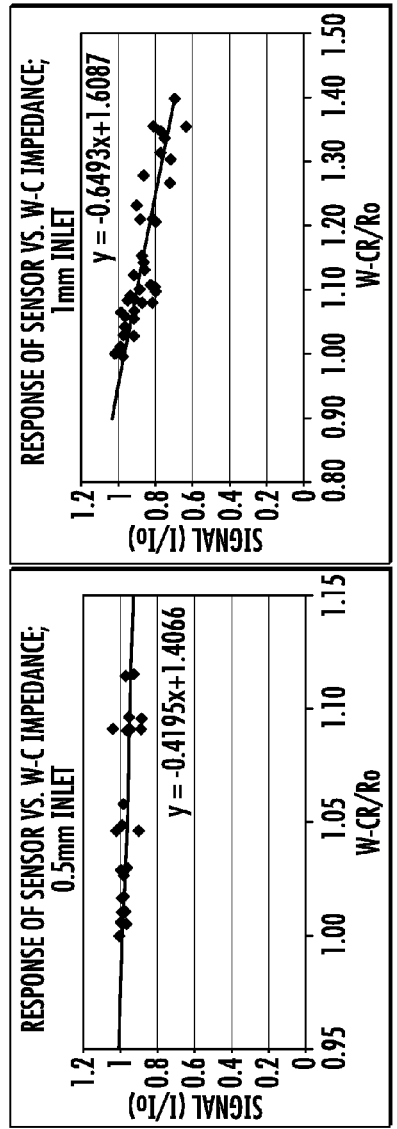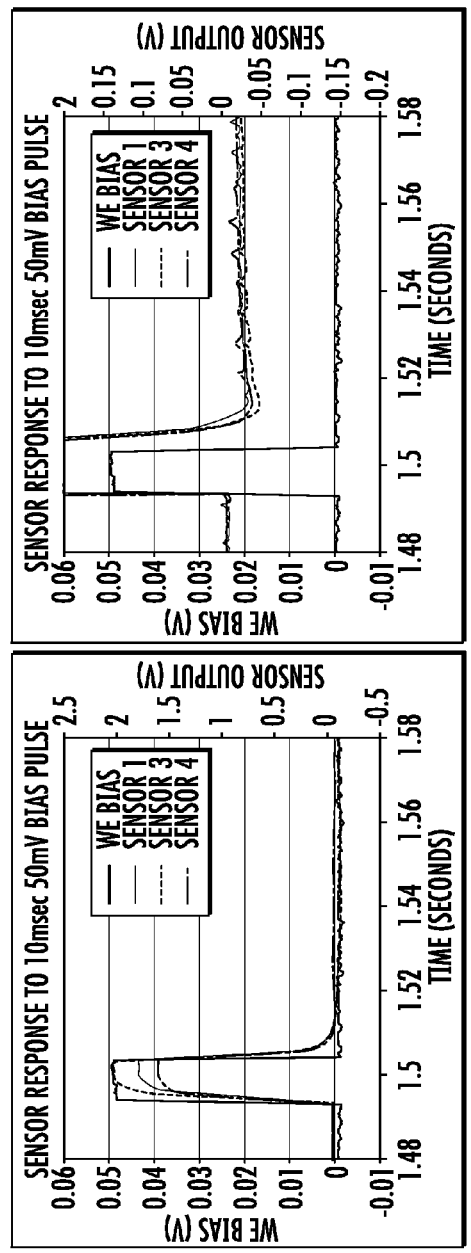

US 9,213,016 B1

AUTOMATED SELF-COMPENSATION APPARATUS AND METHODS FOR PROVIDING ELECTROCHEMICAL SENSORS

BACKGROUND

1. Field

Embodiments provided herein generally relate to automated self-compensation apparatus and methods for providing electrochemical sensors, and particularly to making measurements of gases with electrochemical sensors of the type marketed worldwide for electrochemically active gases.

2. Technical Background

There is currently a need for making measurements of gases with amperometric (electrochemical) sensors for electrochemically active (ox-redox) gases. The current sensors may respond to a target gas, such as carbon monoxide (CO), oxygen, hydrogen sulfide ($H_2S$), etc. and also to changes of an environmental factor, such as changes in temperature (T), pressure (P), and relative humidity (RH) that fluctuate depending on the day, weather, and user situation. In many current solutions, the temperature coefficient is measured in an environmental chamber by calibrating a CO sensor at different temperatures and then measuring the effect of temperature on the signal.

While these solutions may provide some improvement to previous designs, the signal and background also vary with relative humidity and such variation can be realized as a slow change measured over hours, days, weeks, or months. Currently there is no way to correct for such drift. Many current sensor manufacturers go to great lengths to design sensors to minimize this effect by using extremely large electrolyte reservoirs and very small gas access ports. Again, while these solutions may have some benefits, these designs result in bulky sensors, added expense, low sensitivity, poor performance, and inevitable failure.

SUMMARY

In one embodiment, an apparatus for self-compensation may include an electrochemical sensor device that detects the presence of a predetermined gas, where the electrochemical sensor device includes a potentiostat. The apparatus may also include a pulse generator that is coupled to the electrochemical sensor device, the pulse generator generating an electrical signal, and a data acquisition and calculation module that is coupled to the electrochemical sensor device and the pulse generator. The data acquisition and calculation module may include a memory component that stores logic that, when executed by a processor, causes the automated self-compensating apparatus to measure a signal from the electrochemical sensor device, wherein the signal relates to the presence of the predetermined gas, measure an internal property of the electrochemical sensor device by electronically pinging the potentiostat, and receive a response from the potentiostat. The logic may also cause the apparatus to interpret the response through an associative relationship between the electrochemical sensor device and the data acquisition and calculation module, determine an effect of an environmental factor from the response, compensate for effects of the environmental factor by adjusting the signal from the electrochemical sensor device, and output the adjusted signal.

In another embodiment, a method that may include measuring a signal from an electrochemical sensor device, where the signal relates to the presence of a predetermined gas, and where the electrochemical sensor device includes a potentiostat, measuring an internal property of the electrochemical sensor device by electronically pinging the potentiostat, and receiving a response from the potentiostat. In some embodiments, the method may include interpreting the response through an associative relationship between the electrochemical sensor device and a data acquisition and calculation module, determining an effect of an environmental factor from the response, compensating for effects of the environmental factor by adjusting the signal from the electrochemical sensor device and outputting the adjusted signal.

These and additional features provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

FIGS. 6A-6D depict electrolyte concentration, according to one or more embodiments shown and described herein;

FIGS. 10A-10B depict sensor response, according to one or more embodiments shown and described herein;

FIGS. 11A-11B depict sensor response versus bias pulse, according to one or more embodiments shown and described herein;

DETAILED DESCRIPTION

Embodiments described herein are configured to provide a mechanism (such as an automated self-compensating apparatus) for compensation of drift parameters. The mechanism frees up design rules, allows lower cost and smaller sensors to be made and achieve high accuracy over long times even at low levels. Accordingly, embodiments may be configured to accomplish this two ways: using an environmental sensor, such as a relative humidity sensor, a pressure sensor, a thermometer, and/or other similar sensor in combination with the gas sensor and/or using a novel process based on measurement of the internal properties of the electrochemical sensor device, which have been uniquely isolated and identified as a property/measurement made in a certain way that can represent the effect of an environmental sensor on the gas sensors and thereby be used to compensate for the effects of environmental factors, such as relative humidity (e.g., the RH drift) in a given gas sensor. Additionally, embodiments of this apparatus may be embodied into other devices, such as a mobile phone, a wireless sensor network, and/or other devices.

Accordingly, embodiments include a mechanism for measuring electrochemical sensor signals, measuring an internal property of the sensor (such as by electronically measuring under uP control), automatically stimulating or pinging the potentiostat, receiving a response from the potentiostat, reading the result of the ping, interpreting the result of the ping for the sensor through a unique associative and cause and effect relationship, and implementing an algorithm to determine and compensate for the effects of relative humidity on an electrochemical sensor signal.

This has the beneficial effect of compensating zero and span of the sensor for long term and short term environmental effects, such as relative humidity effects and vastly improving the accuracy of the sensor over its lifetime. Because the sensor will be accurate for longer times, there is less frequent or no calibration and maintenance required thus saving money, improving performance, and benefiting applications for these types of sensors.

Additionally, it should be understood that while embodiments described herein depict the implementation for an aqueous electrolyte (such as $H_2SO_4$) and CO sensing with several amperometric electrochemical sensors for CO in the 0-1000 ppm range, the approach is easily seen to extend to other sensory systems employing other sensors with different electrolyte, electrodes and geometries.

It should also be understood that other gases may be detected via the embodiments described herein. As an example, embodiments may be configured to detect $H_2S$, $O_3$, $NO_2$, ethanol and/or other gases.

Figure 1A:
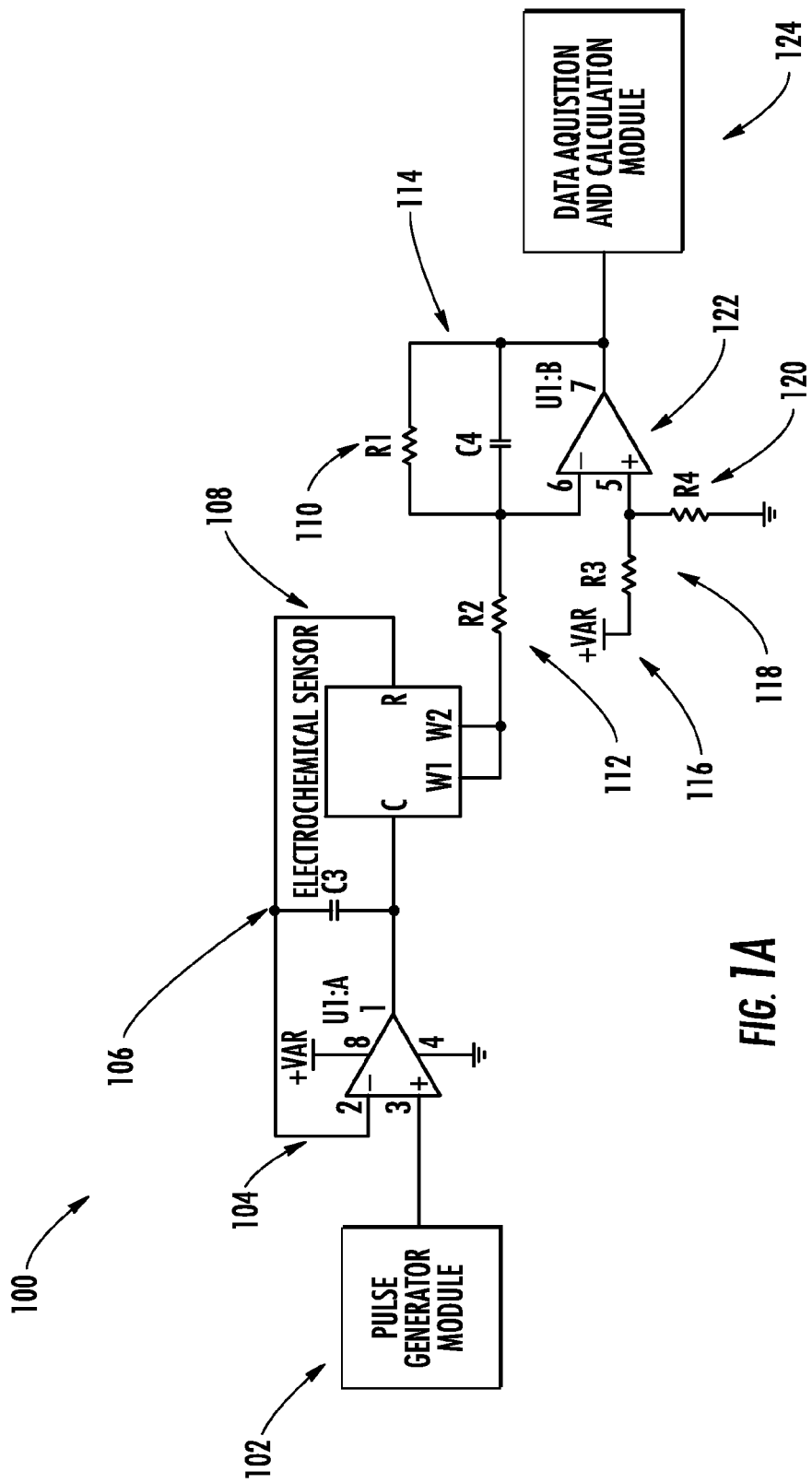
FIGS. 1A, 1B depict a circuit for providing self compensation, according to one or more embodiments shown and described herein.
Figure 1B:
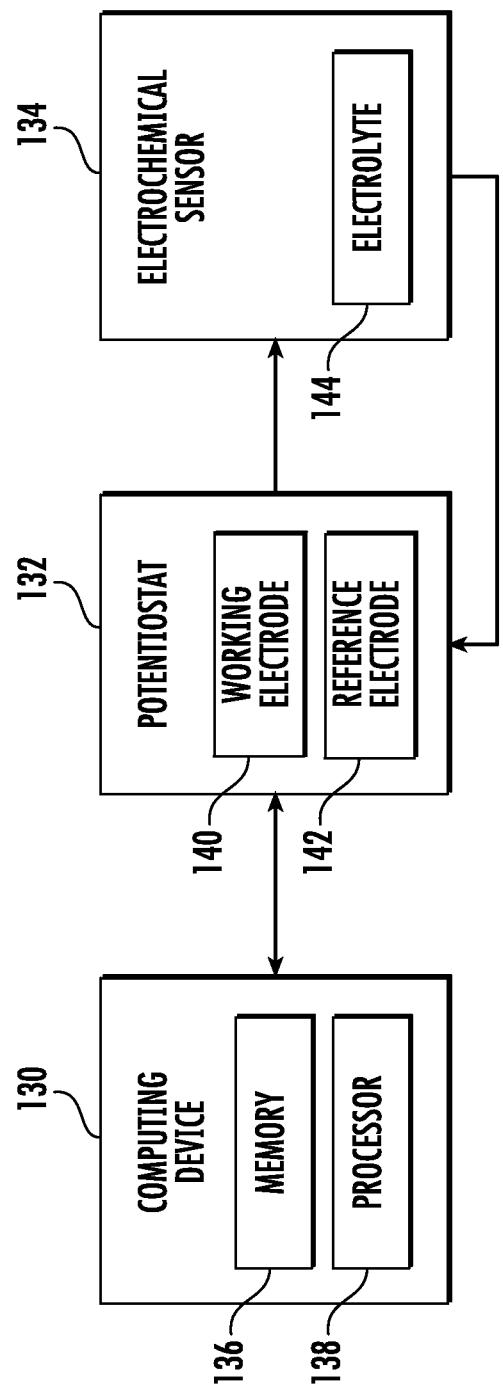

Referring now to the drawings, FIGS. 1A, 1B depict a circuit 100 for providing self compensation, according to one or more embodiments shown and described herein. As illustrated in FIG. 1A, the circuit 100 includes a pulse generation module 102 for generating input pulses to the circuit 100. The pulse voltage generator can include an algorithm in firmware that a microprocessor can execute and execute to the potentiostat. An operational amplifier 104 is also included and receives input from the pulse generation module 102, as well as a feedback loop. Depending on the embodiment, the operational amplifier may be embodied as the potentiostat operational amplifier itself. FIG. 1 also illustrates that some embodiments may include a capacitor 106 that is connected in parallel with an electrochemical sensor device 108. The electrochemical sensor device 108 may include one or more gas ports, a reservoir or surface for receiving an electrolyte, a gas sensor, an environmental sensor (such as a relative humidity sensor, a thermometer, a pressure sensor, etc.), a potentiostat (which may be constructed from discrete parts and/or an asynchronous integrated circuit (SSIC) such as LMP91000 From Texas Instruments), and/or one or more other components. The gas port(s) may vary in size, depending on the embodiment. Additionally, the gas sensor may be configured to sense the presence of a predetermined gas. The environmental sensor may be configured to detect the presence of a predetermined environmental factor. The electrochemical sensor device 108 is also coupled to a second resistor 112, in series with a first resistor 110, a capacitor 114, and an operational amplifier 122. Also coupled to the operational amplifier 122 is a variable input 116, as well as resistors 118 and 120. The operational amplifier 122 is also coupled to a data acquisition and calculation module 124. The data is sent to the processor that executes an algorithm to calculate corrections to improve accuracy of the sensory reading and compensate for environmental variables.

The electrochemical sensor device 108 may be configured to measure the concentration of a predetermined gas. As an example, the electrochemical sensor device 108 may be configured to detect the presence of carbon monoxide (CO) or other gas. Additionally, the data acquisition and calculation module 124 may be configured as a computing device and thus may include a memory component (with volatile and/or nonvolatile memory devices) for storing logic and/or a processor for executing logic. Depending on the particular embodiment, the data acquisition and calculation module 124 may include components, such as input/output, display hardware, communication hardware, and/or other components of a computing device. Similarly, the logic be hardware, software, and/or firmware (depending on the embodiment) and may be configured to account for environmental drift, such as from relative humidity, temperature, pressure, etc. In some embodiments, the data acquisition and calculation module 124 may provide a general protocol for pinging a reference voltage to a potentiostat of the electrochemical sensor device 108 and reading resultant return signal. The data acquisition and calculation module 124 may additionally calculate an area, height, and/or capacitive signal that relates to impedance and thus to concentration of the electrolyte. This information may provide insight to dry-out and the relative humidity effect on the drift of the electrochemical sensor device 108. Based on this calculation, the data acquisition and calculation module 124 may adjust a reading from the electrochemical sensor device 108 according the drift.

It should also be understood that the electrochemical sensor device 108 may include an electrochemical cell (or gas sensor) for measurement of CO and other gases. A SPEC brand sensor may be utilized because it has a small reservoir and relative humidity effects are easy to observe and correct by this process. However, even sensors with large electrolyte volumes and slow relative humidity effects on electrolyte volume (e.g., small holes and small signals and low sensitivity) will behave this way.

In more general terms of FIG. 1B, the circuit 100 may include a computing device 130, a potentiostat 132, and an electrochemical sensor 134. The computing device 130 may include a memory 136, a processor 138, data storage, an operating system, and/or other hardware, software, and firmware for performing the desired functionality. Accordingly, the computing device 130 may be utilized as a pulse generator, such as to provide the functionally described with regard to the pulse generator 102 from FIG. 1A. In such an embodiment, the computing device 130 may include hardware, software, and/or firmware to control the potentiostat bias for facilitating a ping in a controlled manner and read the resulting effect on the signal to measure a signal related to relative humidity effect. Additionally, the potentiostat 132 may include a working electrode 140, a reference electrode 142, and/or other software, hardware, or firmware for performing the functionality described above with regard to the circuit 100, which includes the operational amplifier 104. As described above, the computing device 130 and the potentiostat 132 may engage in two-way communication. Additionally, the potentiostat 132 may ping the electrochemical sensor 134 and may receive feedback from the electrochemical sensor 134 for adjusting sensor readings based on relative humidity and/or other environmental factors.

Pinging the electrochemical sensor 134 may include changing a potential at the working electrode 140 or the reference electrode 142 and then changing the potential back to its original voltage. By determining the output of the potentiostat, a determination may be made regarding whether a double layer capacitance in the electrochemical sensor 134 is mobile at the electrode surface. The double layer capacitance will additionally change with a concentration of an electrolyte 144 in the electrochemical sensor 134. Because the relative humidity affects the concentration of the electrolyte 144, compensations may be made based on changes to the concentration of the electrolyte.

Figure 2:
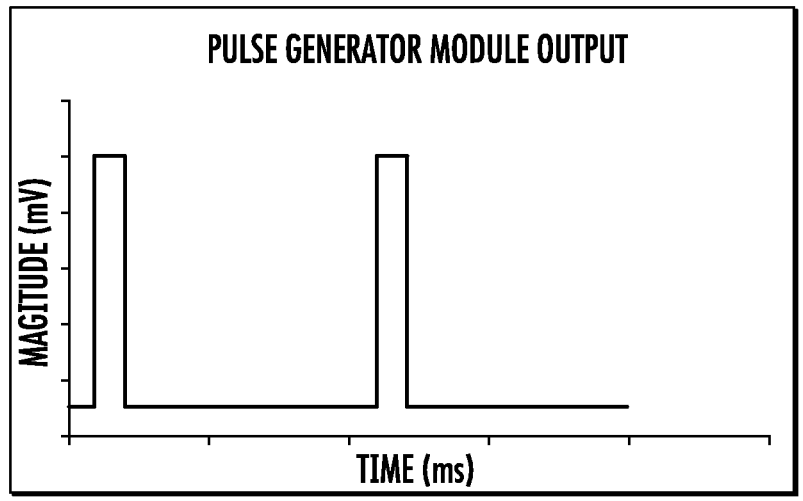
FIG. 2 depicts a pulse generator module response of a self compensation device, according to one or more embodiments shown and described herein.

FIG. 2 depicts a pulse generation module 102 response of a self compensation device, according to one or more embodiments shown and described herein. As illustrated, an electrical signal and/or pulse of any offset, any amplitude, any duration, and any duty cycle, generated by the pulse generation module 102, may be generated to cause a characteristic electrochemical sensor response of the electrochemical sensor device 108 that is a function of electrolyte concentration.

Figure 3:
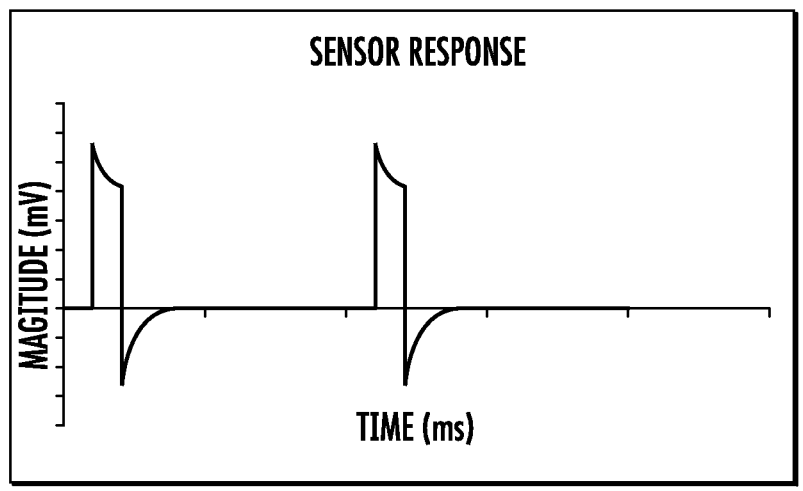
FIG. 3 depicts a sensor response for a self compensation, according to one or more embodiments shown and described herein.

FIG. 3 depicts a sensor response for a self compensation, according to one or more embodiments shown and described herein. In response to the pulse generation module 102 generating the pulse form FIG. 2, the electrochemical sensor device 108 may provide the depicted sensor response. Parameters of the sensor response, such as initial magnitude, decay constant, and integration area may be used as part of the algorithm to compensate the sensor response for short and long term relative humidity effects and electrolyte dry-out.

The concentration of the electrolyte increases when the electrolyte is exposed to low relative humidity for extended periods of time. This results in the electrolyte (e.g. the acid) increasing concentration or molarity. The different molarity results in a different double layer impedance and this is reflected in the changing characteristics observed during the "ping" of the potentiostat-electrochemical sensor cell. This "ping" can then be related to the concentration of the electrolyte. Since the sensor signal is a function of the electrolyte concentration (see FIGS. 4C, 4D, and 5 for example) then one can correct the sensor zero and span for the changes in signal cause by relative humidity.

Figure 4A:
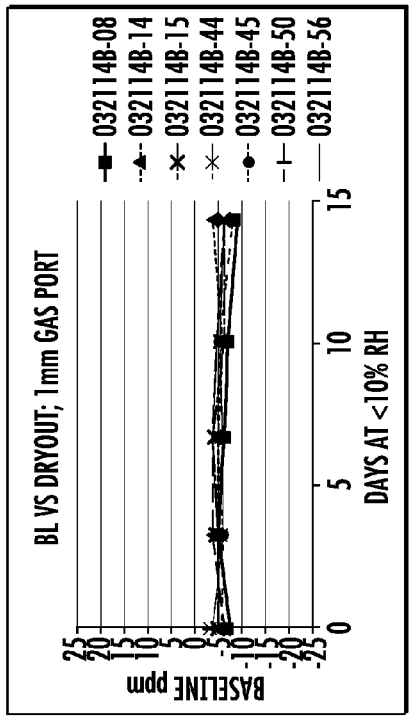
FIGS. 4A-4D depict graphical representations for dry-out and response characteristics, according to one or more embodiments shown and described herein.
Figure 4C:
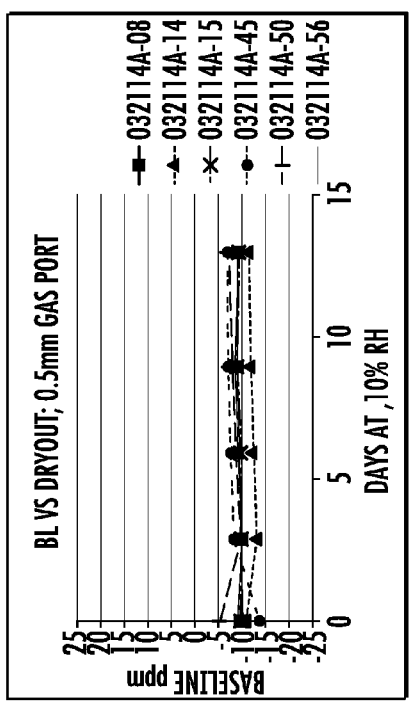
Figure 4B:
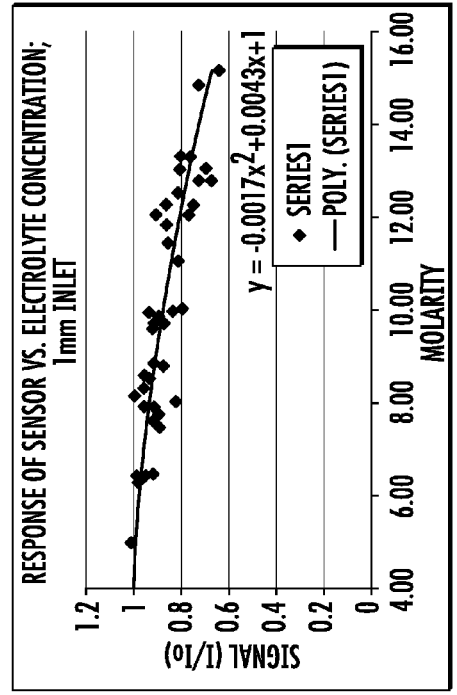
Figure 4D:
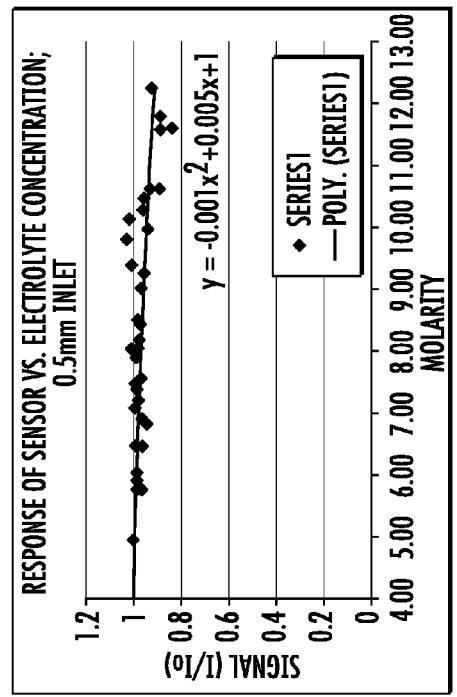

FIGS. 4A-4D depict graphical representations for dry-out and response characteristics, according to one or more embodiments shown and described herein. Specifically, FIG. 4A depicts a baseline parts per million of a predetermined gas on the y-axis, while the x-axis provides a time period what the ambient was at less than 10% relative humidity or a electrochemical sensor device 108 with a 0.5 millimeter gas port. FIG. 4B depicts the same information on an electrochemical sensor device 108 with a 1.0 millimeter gas port. FIG. 4C depicts the response of a sensor versus electrolyte concentration for an electrochemical sensor that has a 0.5 millimeter inlet. FIG. 4D depicts the same information with a 1.0 millimeter inlet.

It can be seen that the magnitude of the effect of dry-out is controlled by the diameter of the gas port (more specifically by the ratio of electrode catalyst sites to the number of analyte molecules reaching the working electrode). It is also clear that in any geometry, $I/I_0$ is directly proportional to $R/R_0$ ($R_0$ is the initial internal impedance of the sensor, slightly different for each sensor of the same type and perhaps vastly different for different types), thus allowing a direct mechanism for compensating the sensor response for "dry-out": for example: applying a brief "pulse" to the WE bias, and from sensor response parameters such as initial magnitude, time constant of the decay, and integration area can be used in a compensation algorithm to correct the sensor response for short and long term relative humidity effects, electrolyte "dry-out", or any other parameters which may affect the impedance of the sensor.

Figure 5:
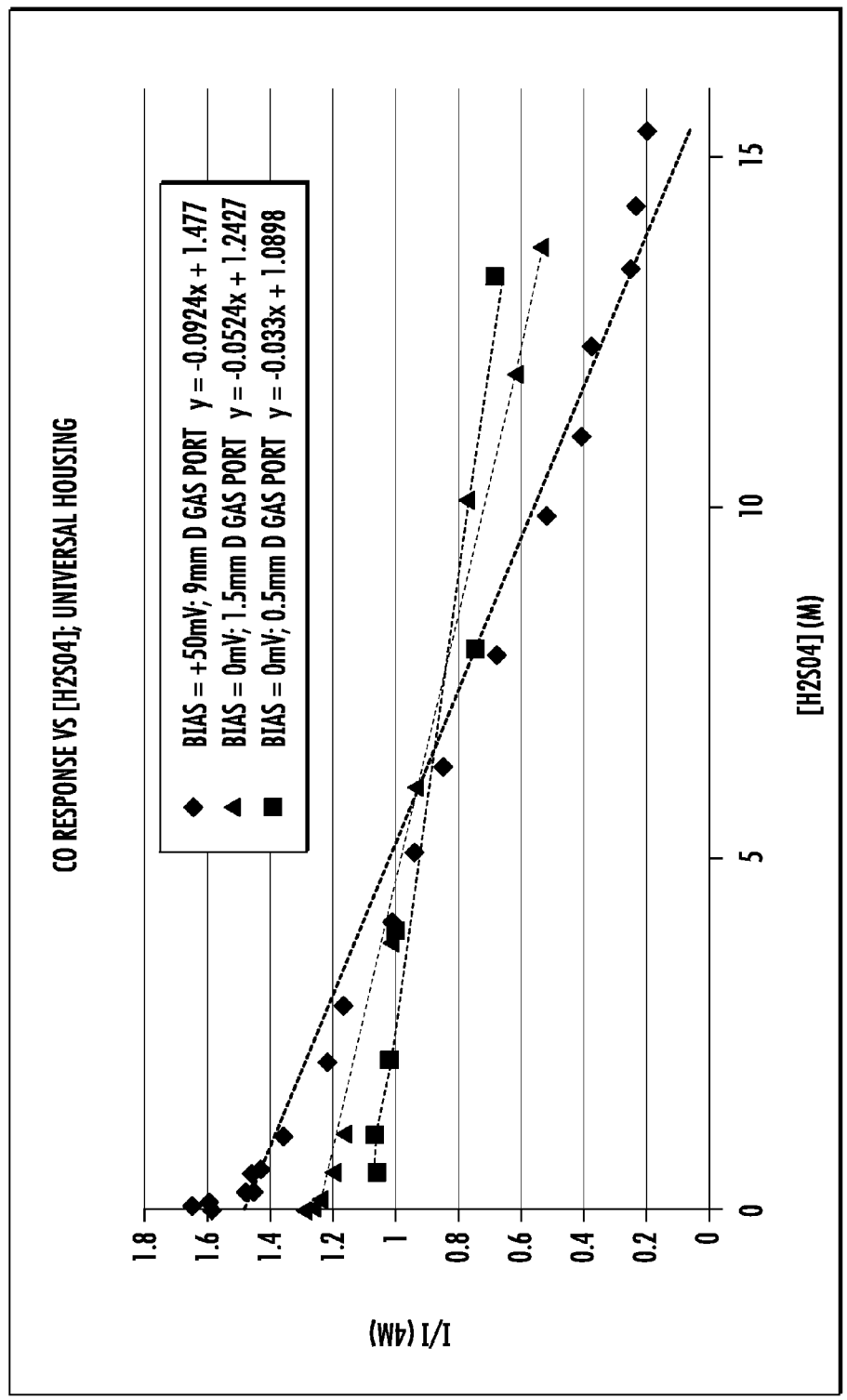
FIG. 5 depicts CO response versus $H_2SO_4$ in a universal housing, according to one or more embodiments shown and described herein.

FIG. 5 depicts CO response versus $H_2SO_4$ in a universal housing, according to one or more embodiments shown and described herein. As illustrated, the data may be collected in "universal housing" bulk electrolyte of varying concentration. Additionally, the data with 0.5 millimeter port and 1 millimeter port are very similar to that obtained from SPEC sensor with same diameter gas ports.

FIGS. 6A-6D depict electrolyte concentration, according to one or more embodiments shown and described herein. As illustrated, FIG. 6A depicts electrolyte concentration (moles) on the y-axis and depicts days that the electrochemical sensor device 108 has been exposed to a relative humidity less than 10%. FIG. 6B is similar to FIG. 6A, except that the electrochemical sensor device 108 used for the data in FIG. 6A utilizes a 0.5 millimeter gas port. FIG. 6B utilizes a 1.0 millimeter gas port. Similarly, FIG. 6C utilizes a 0.5 millimeter gas port, except that instead of 26 micro-liter electrolyte volume, FIG. 6C utilizes 13 micro-liter. FIG. 6D utilizes 1.0 millimeter gas port and a 13 micro-liter electrolyte volume.

Figure 7A:
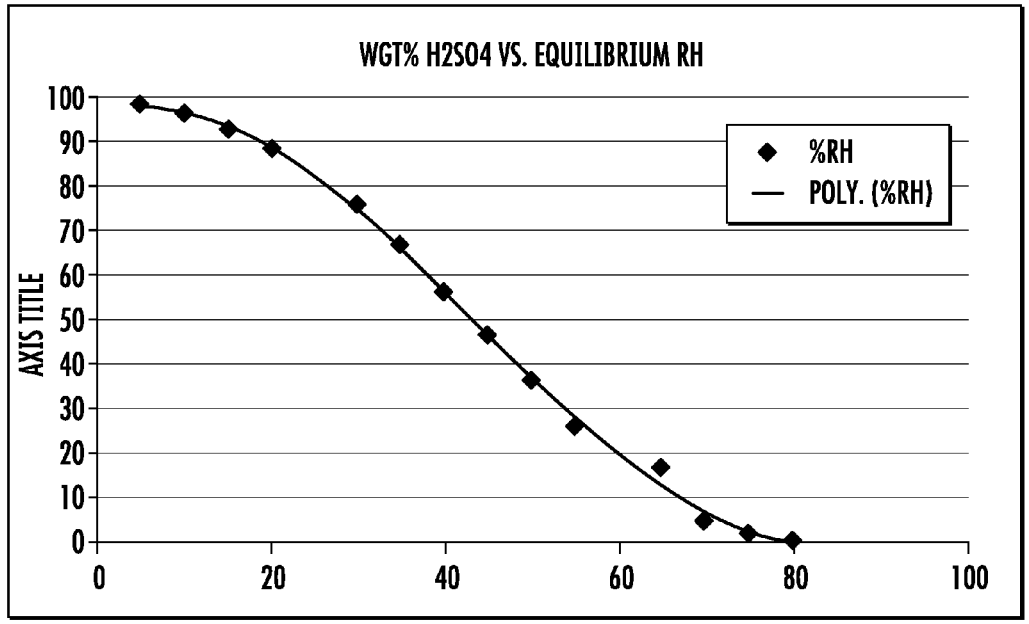
FIGS. 7A-7B depict equilibrium relative humidity, according to one or more embodiments shown and described herein.
Figure 7B:
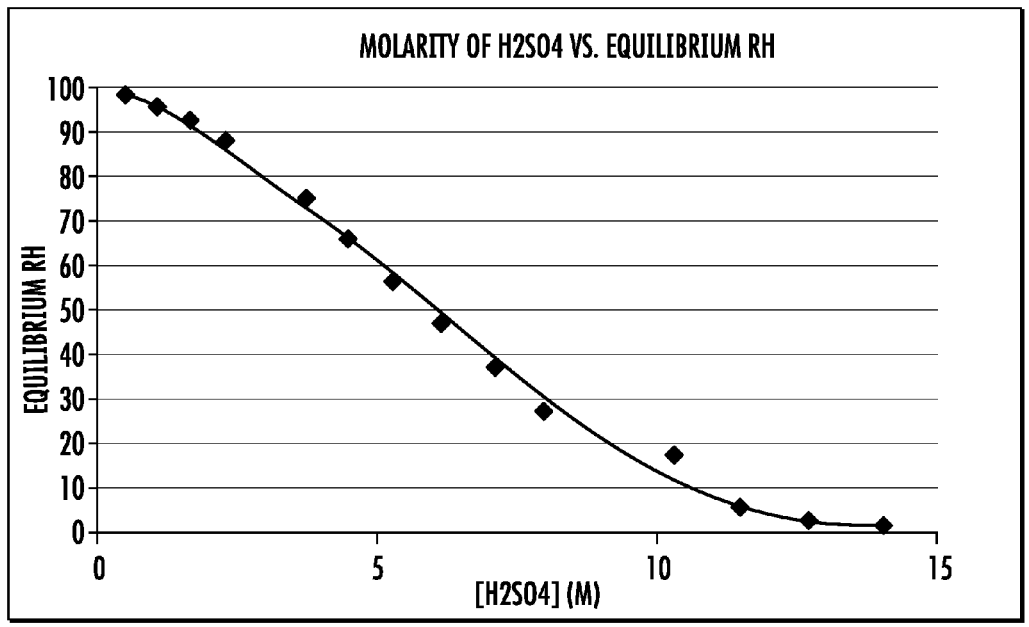

FIGS. 7A-7B depict equilibrium relative humidity, according to one or more embodiments shown and described herein. Specifically, FIG. 7A depicts a weight percentage of the electrolyte $H_2SO_4$ versus equilibrium relative humidity. FIG. 7B depicts the molarity of the electrolyte $H_2SO_4$ versus equilibrium relative humidity.

Figure 8:
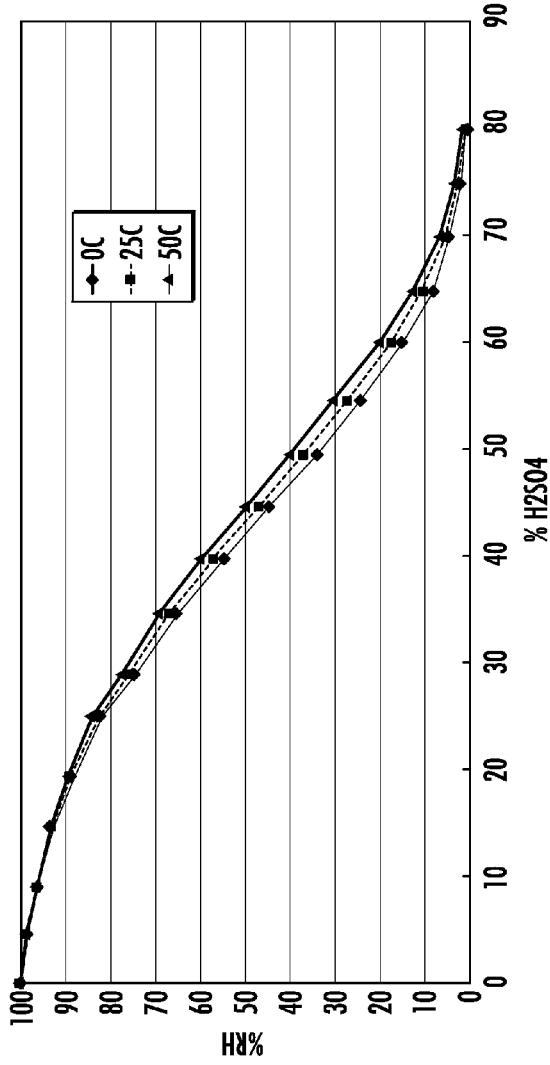
FIG. 8 depicts relative humidity versus $H_2SO_4$, according to one or more embodiments shown and described herein.

FIG. 8 depicts relative humidity versus $H_2SO_4$, according to one or more embodiments shown and described herein. Specifically, FIG. 8 depicts $H_2SO_4$ versus equilibrium relative humidity and illustrates that this is essentially independent of temperature.

Figure 9A:
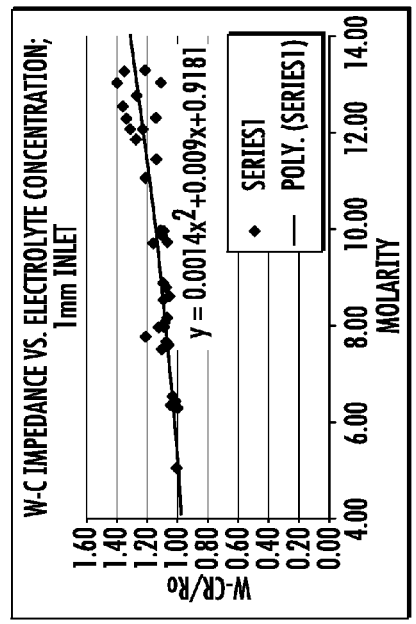
FIGS. 9A-9B depict W-C impedance versus electrolyte concentration, according to one or more embodiments shown and described herein.
Figure 9B:
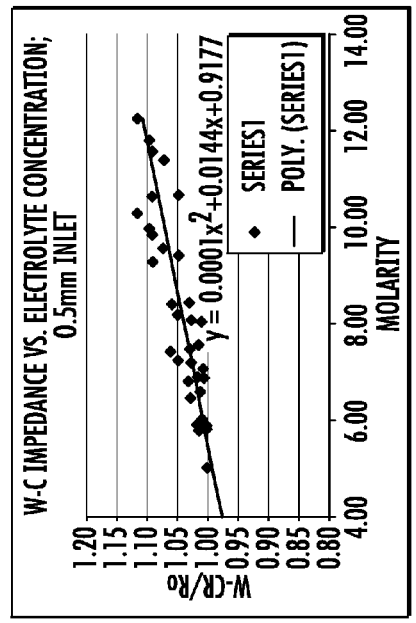

FIGS. 9A-9B depict W-C impedance versus electrolyte concentration, according to one or more embodiments shown and described herein. Specifically, FIG. 9A illustrates data associated with an electrochemical sensor device 108 with a 0.5 millimeter inlet. FIG. 9B depicts data related to an electrochemical sensor device 108 with a 1.0 millimeter inlet. The relationship between CO response and electrolyte concentration is also shown. The relationship between $H_2SO_4$ and cell impedance as measured between the WE and CE) is also shown.

It can be seen that the magnitude of the effect of dry-out is controlled by the diameter of the gas port and more specifically by the ratio of electrode catalyst sites to the number of analyte molecules reaching the working electrode. It is also clear that in any geometry, $I/I_0$ is directly proportional to $R/R_0$, thus allowing a direct mechanism for compensating the sensor response for "dry-out." For example, applying a brief "pulse" to the WE bias, and from sensor response parameters such as initial magnitude, time constant of the decay, and integration area can be used in a compensation algorithm to correct the sensor response for short and long term relative humidity effects, electrolyte dry-out, or any other parameters which may affect the impedance of the electrochemical sensor device 108. There are additional implications of using the described apparatus and method to understand behavior of the sensor with respect to its drift and response and improvements in accuracy and such data will also be useful in compensating for response times, sensitivities, selectivities, and stabilities.

FIGS. 10A-10B depict sensor response, according to one or more embodiments shown and described herein. Specifically, FIG. 10A depicts response of the sensor versus W-C impedance with a 0.5 millimeter inlet. FIG. 10B depicts the same type of information with a 1.0 millimeter inlet. Further, the relationship between the (normalized) sensor response and (normalized) internal impedance is shown. Embodiments may also depict sensor response to 10 milli-seconds with a 50 milli-volt bias pulse.

FIG. 11A-11B depict sensor response versus bias pulse, according to one or more embodiments shown and described herein. Specifically, FIGS. 11A and 11B depict that BL recovers within 500 milli-seconds of a 10 milli-second pulse. Three sensors with about 25% different peak value all recover to BL with about the same time constant.

Figure 12:
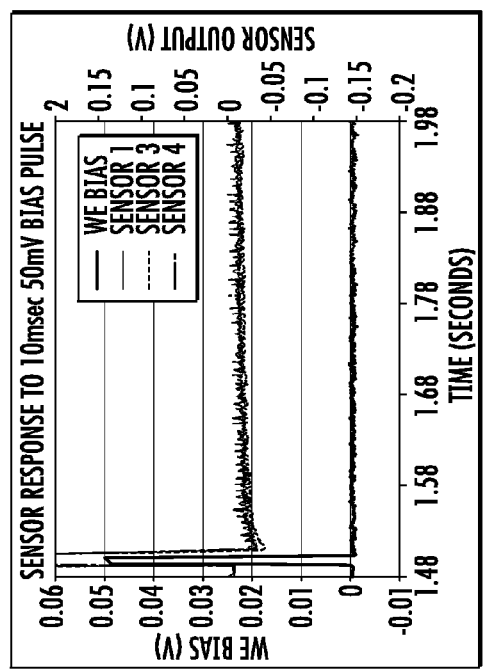
FIG. 12 depicts a sensor response versus bias pulse over a second set of outputs, according to one or more embodiments shown and described herein.

FIG. 12 depicts a sensor response versus bias pulse over a second set of outputs, according to one or more embodiments shown and described herein. Similar to FIGS. 11A and 11B, FIG. 12 depicts sensor response to 10 milliseconds of a 50 milli-volt bias pulse.

Figure 13A:
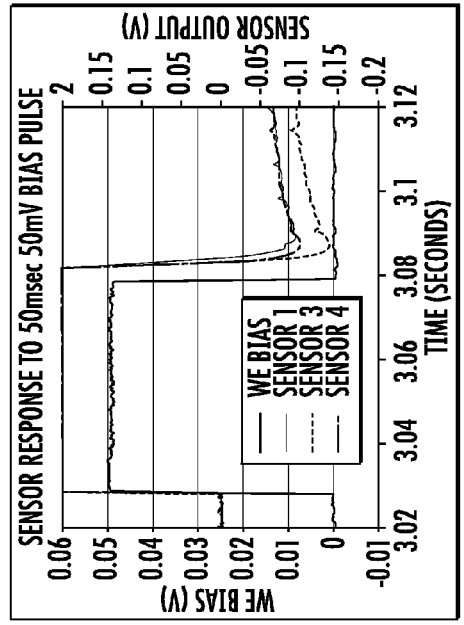
FIGS. 13A-13B depict sensor response versus bias pulse over WE bias voltages.
Figure 13B:
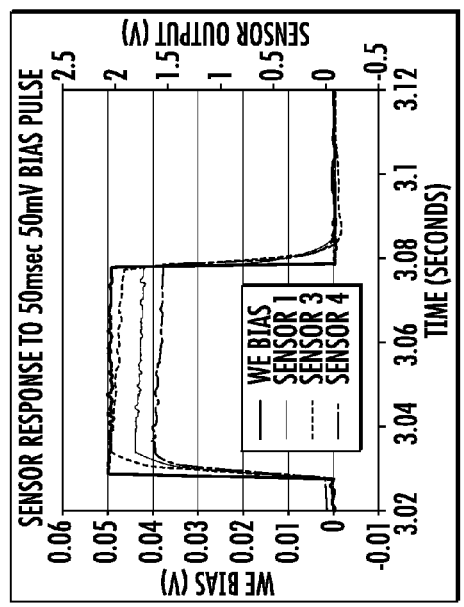

FIGS. 13A-13B depict sensor response versus bias pulse over WE bias voltages. Specifically, FIGS. 13A-13B also detect sensor response to 10 milliseconds of a 50 milli-volt bias pulse.

The size and shape of the pulse depends on the acid concentration and the acid concentration depends on the exposure of the electrochemical sensor device 108. At low relative humidity (e.g. 10% relative humidity), the acid concentration will increase and the pulse dimensions will change in proportion to the increase in acid of the sensor. This is a linear change for many sensors but it does not need to be. The change just needs to be known and measured for a given electrochemical sensor device 108. The change in $R/R_0$ may be about 10-20% increasing over the range 4-10M $H_2SO_4$ solution and the change is signal and background is also about 10-20% decreasing over this range.

Therefore, a compensation algorithm may utilize the pulse and duration to calculate the RC time constant, relate the time constant to the $R/R_0$ ($R_0$ is the initial internal impedance of the sensor, slightly different for each sensor of the same type and perhaps vastly different for different types) and then apply a correction to the span and zero of the sensors to compensate for dry-out or water pick up by the electrolyte due to exposure to variable relative humidity in the environment. This thereby makes the sensor more accurate with less drift which cause inaccuracy, making the sensor more stable and not need calibrations.

Figure 14:
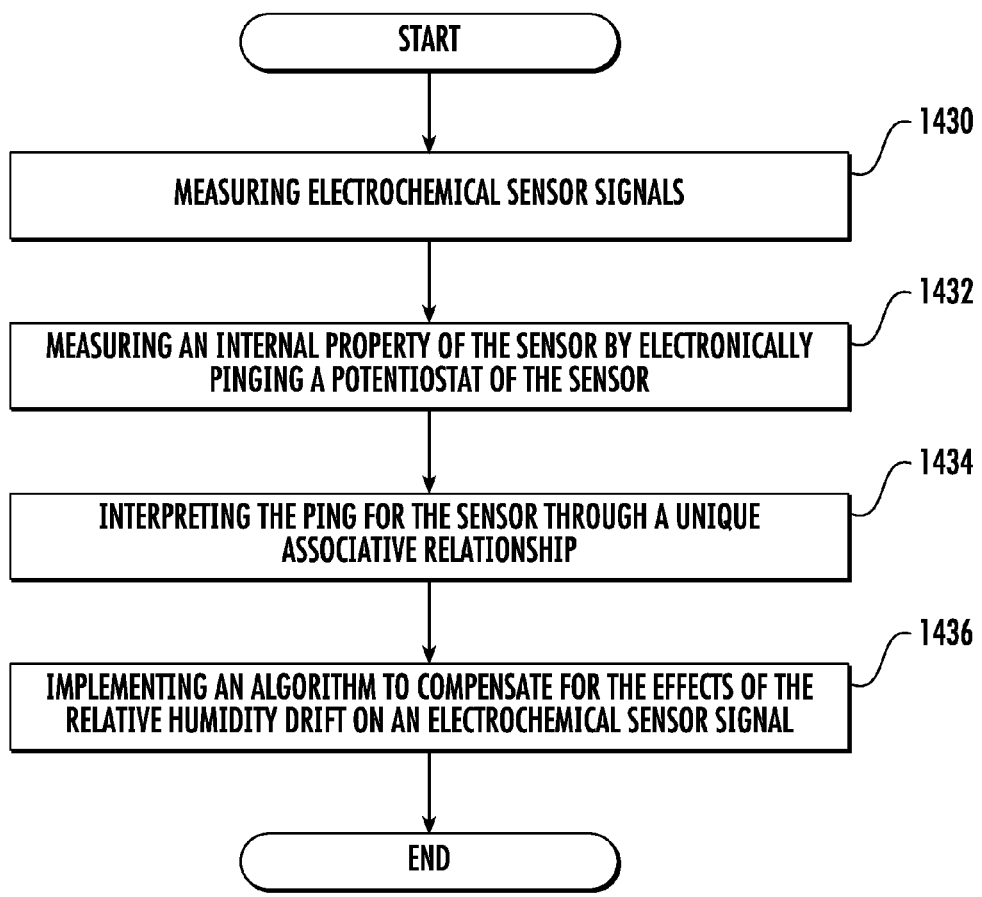
FIG. 14 depicts a flowchart for providing self compensation, according to one or more embodiments shown and described herein.

FIG. 14 depicts a flowchart for providing self compensation, according to one or more embodiments shown and described herein. Specifically, in block 1430, signals from the electrochemical sensor device 108 may be measured. In block 1432, an internal property of the electrochemical sensor device 108 may be measured by pinging a potentiostat of the electrochemical sensor device 108. In block 1434, the ping may be received and interpreted through a unique associative relationship between the electrochemical sensor device 108 and the data acquisition and calculation module 124. In block 1436, an algorithm may be implemented determine the effect of relative humidity on the electrochemical sensor device 108 and compensate for effects of relative humidity on the electrochemical sensor signal to create an adjusted signal. The adjusted signal may then be output to a display and/or to another component for utilizing the adjusted signal.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

What is claimed is:

1. A method for automated self-compensation, comprising:
   measuring, by a processor, a signal from an electrochemical sensor device, wherein the signal relates to the presence of a predetermined gas, and wherein the electrochemical sensor device includes a potentiostat;
   measuring, by the processor, an internal property of the electrochemical sensor device by electronically pinging the potentiostat;
   receiving, by the processor, a response from the potentiostat;
   interpreting, by the processor, the response through an associative relationship between the electrochemical sensor device and a data acquisition and calculation module;
   determining, by the processor, an amount of drift resulting from an environmental factor from the response, wherein determining an amount of drift comprises determining a compensation algorithm that utilizes sensor response parameters from the electrochemical sensor device, including initial magnitude, time constant of decay, and integration area;
   compensating, by the processor, for effects of the environmental factor by adjusting the signal from the electrochemical sensor device; and
   utilizing, by the processor, the adjusted signal.

2. The method of claim 1, wherein the environmental factor includes at least one of the following: relative humidity, temperature, and pressure.

3. The method of claim 1, further comprising storing an electrolyte for utilization by the electrochemical sensor.

4. The method of claim 3, wherein the electrolyte includes $H_2SO_4$.

5. The method of claim 1, wherein the predetermined gas includes at least one of the following: CO, $H_2S$, $O_3$, $NO_2$, NO, $SO_2$, and ethanol.

6. The method of claim 1, further comprising calculating at least one of the following that relates to dry-out and an effect of relative humidity on drift of the electrochemical sensor: an area, a height, and a capacitive signal.

7. A system for automated self-compensation, comprising:
   a device that includes a processor and a memory component, wherein the memory component stores logic is programmed for performing at least the following, when executed by the processor:
   measure a signal from an electrochemical sensor device, wherein the signal relates to the presence of a predetermined gas, and wherein the electrochemical sensor device includes a potentiostat;
   measure an internal property of the electrochemical sensor device by electronically pinging the potentiostat;
   receive a response from the potentiostat;
   interpret the response through an associative relationship between the electrochemical sensor device and a data acquisition and calculation module;
   determine an amount of drift resulting from an environmental factor from the response, wherein determining an amount of drift comprises determining a compensation algorithm that utilizes sensor response parameters from the electrochemical sensor device, including initial magnitude, time constant of decay, and integration area;

compensate for effects of the environmental factor by adjusting the signal from the electrochemical sensor device; and utilize the adjusted signal.

8. The system of claim 7, wherein the environmental factor includes at least one of the following: relative humidity, temperature, and pressure.

9. The system of claim 7, wherein the logic is further programmed for storing an electrolyte for utilization by the electrochemical sensor.

10. The system of claim 7, wherein the electrolyte includes $H_2SO_4$.

11. The system of claim 7, wherein the predetermined gas includes at least one of the following: CO, $H_2S$, $O_3$, $NO_2$, NO, $SO_2$, and ethanol.

12. The system of claim 7, wherein the logic is further programmed for calculating at least one of the following that relates to dry-out and an effect of relative humidity on drift of the electrochemical sensor: an area, a height, and a capacitive signal.

13. An electrochemical sensor apparatus, comprising:
an electrochemical sensor; and
a computer that includes a memory component and a processor, wherein the memory component stores logic that is programmed for performing the following, when executed by the processor:
   measure a signal from an electrochemical sensor device, wherein the signal relates to the presence of a predetermined gas, and wherein the electrochemical sensor device includes a potentiostat;
   measure an internal property of the electrochemical sensor device by electronically pinging the potentiostat;
   receive a response from the potentiostat;
   interpret the response through an associative relationship between the electrochemical sensor device and a data acquisition and calculation module;
   determine an amount of drift resulting from an environmental factor from the response, wherein determining an amount of drift comprises determining a compensation algorithm that utilizes sensor response parameters from the electrochemical sensor device, including initial magnitude, time constant of decay, and integration area;
   compensate for effects of the environmental factor by adjusting the signal from the electrochemical sensor device; and
   utilize the adjusted signal.

14. The electrochemical sensor apparatus of claim 13, wherein the environmental factor includes at least one of the following: relative humidity, temperature, and pressure.

15. The electrochemical sensor apparatus of claim 13, wherein the logic is further programmed for storing an electrolyte for utilization by the electrochemical sensor.

16. The electrochemical sensor apparatus of claim 13, wherein the electrolyte includes $H_2SO_4$.

17. The electrochemical sensor apparatus of claim 13, wherein the predetermined gas includes at least one of the following: CO, $H_2S$, $O_3$, $NO_2$, NO, $SO_2$, and ethanol.

18. The electrochemical sensor apparatus of claim 13, wherein the logic is further programmed for calculating at least one of the following that relates to dry-out and an effect of relative humidity on drift of the electrochemical sensor: an area, a height, and a capacitive signal.

* * * * *